US012616685B2

(12) United States Patent (10) Patent No.: US 12,616,685 B2

Hunt et al. (45) Date of Patent: May 5, 2026

(54) CONCOMITANT ADMINISTRATION OF GLUCOCORTICOID RECEPTOR MODULATOR RELACORILANT AND CYP2C9 SUBSTRATES

(71) Applicant: Corcept Therapeutics Incorporated, Menlo Park, CA (US)

(72) Inventors: Hazel Hunt, Storrington (GB); Joseph Custodio, Menlo Park, CA (US)

(73) Assignee: Corcept Therapeutics Incorporated, Menlo Park, CA (US)

( * ) Notice: Subject to any disclaimer, the term of this patent is extended or adjusted under 35 U.S.C. 154(b) by 294 days.

(21) Appl. No.: 17/330,987

(22) Filed: May 26, 2021

(65) Prior Publication Data

US 2021/0369689 A1 Dec. 2, 2021

Related U.S. Application Data

(60) Provisional application No. 63/030,809, filed on May 27, 2020.

(51) Int. Cl.
*A61K 31/444* (2006.01)
*A61K 31/337* (2006.01)
*A61K 31/64* (2006.01)

(52) U.S. Cl.
CPC .......... *A61K 31/444* (2013.01); *A61K 31/337* (2013.01); *A61K 31/64* (2013.01)

(58) Field of Classification Search
None
See application file for complete search history.

(56) References Cited

U.S. PATENT DOCUMENTS

| | | | | |
|---|---|---|---|---|
| 11,058,670 B2 * | 7/2021 | Moraitis | ............ | A61K 31/4745 |
| 11,464,764 B2 * | 10/2022 | Scott | .................... | A61K 9/4808 |
| 11,590,113 B2 * | 2/2023 | Moraitis | ............ | A61K 31/4745 |
| 11,684,612 B2 * | 6/2023 | Moraitis | ............ | A61K 31/4745 |
| | | | | 514/293 |
| 11,925,626 B2 * | 3/2024 | Scott | .................... | A61K 47/34 |
| 2007/0015687 A1 | 1/2007 | Szillvassy et al. | | |
| 2019/0083486 A1 | 3/2019 | Hunt | | |
| 2019/0111036 A1 | 4/2019 | Molina | | |
| 2020/0147065 A1 | 5/2020 | Moraitis | | |

FOREIGN PATENT DOCUMENTS

| | | |
|---|---|---|
| JP | 2018524562 A | 8/2018 |
| JP | 2019507159 A | 3/2019 |
| JP | 2019530666 A | 10/2019 |
| KR | 20150021955 A | 3/2015 |
| WO | 2004009017 A2 | 1/2004 |
| WO | 2004111015 A1 | 12/2004 |
| WO | 2005072132 A2 | 8/2005 |
| WO | 2005072729 A1 | 8/2005 |
| WO | 2005072732 A1 | 8/2005 |
| WO | 2018160775 A1 | 9/2018 |
| WO | 2018183947 A1 | 10/2018 |
| WO | 2018191283 A1 | 10/2018 |
| WO | 2020097513 A1 | 5/2020 |

OTHER PUBLICATIONS

Pivonello et al. "Efficacy and Safety of the Selective Glucocorticoid Receptor Modulator, Relacorilant (up to 400 mg/day), in Patients with Endogenous Hypercortisolism: Results from an Open-Label Phase 2 Study". American Association of Clinical Endocrinologists Annual Congress, Apr. 24-28, 2019. (Year: 2019).*

STAT Rx USA LLC Glimeperide Tablets, USP 2 mg. Published Mar. 2012. pp. 1-14. (Year: 2012).*

"Study of Relacorilant in Combination with Nab-Paclitaxel for Patients with Recurrent Platinum-Resistant Ovarian, Fallopian Tube, or Primary Peritoneal Cancer", ClinicalTrials.gov, Available Online at: www.clinicaltrials.gov/ct2/show/NCT03776812, Accessed from internet on Apr. 30, 2019, 11 pages.

Custodio et al., "An In Vitro and In Vivo Evaluation of the Effect of Relacorilant on the Activity of Cytochrome P450 Drug Metabolizing Enzymes", The Journal of Clinical Pharmacology, vol. 61, Issue 2, Feb. 2021, pp. 244-253.

PCT/US2021/034338 , "International Search Report and Written Opinion", Sep. 13, 2021, 13 pages.

International Patent Application No. PCT/US2021/034338 , "International Preliminary Report on Patentability", Dec. 8, 2022, 7 pages.

"Clinical Drug Interaction Studies—Study Design, Data Analysis, and Clinical Implications Guidance for Industry", U.S. Department of Health and Human Services Food and Drug Administration Center for Drug Evaluation and Research (CDER), Oct. 2017.

(Continued)

*Primary Examiner* — Leslie A. Royds Draper

(74) *Attorney, Agent, or Firm* — Kilpatrick Townsend & Stockton LLP

(57) ABSTRACT

Relacorilant is useful in the treatment of hypercortisolism and cancer. Many drugs useful in treating hypercortisolism or cancer are metabolized by CYP2C9 enzymes. The effects of concomitant administration of relacorilant and a CYP2C9 substrate are disclosed herein.

Relacorilant potently inhibited CYP2C9 in an in vitro test, indicating that co-administration of relacorilant and a CYP2C9 substrate would be expected to increase the CYP2C9 substrate plasma exposure more than five-fold in vivo. Significant reductions in CYP2C9 substrate doses would be expected to be required when administered with relacorilant.

Surprisingly, no such increase in plasma exposure was seen in human studies. Applicant discloses that relacorilant may be safely co-administered with unmodified doses of a CYP2C9 substrate such as, e.g., tolbutamide, glimepiride, and glipizide. Relacorilant and unmodified doses of CYP2C9 substrate such as tolbutamide, glimepiride, and glipizide may be co-administered to treat hypercortisolism, or may be co-administered to a cancer patient.

9 Claims, 1 Drawing Sheet

(56)  References Cited

OTHER PUBLICATIONS

Del Re et al., "The role of drug-drug interactions in prostate cancer treatment: Focus on abiraterone acetate/prednisone and enzalutamide", Cancer Treatment Reviews 55 (2017) 71-82.

Gibbons et al., "Pharmacokinetic Drug Interaction Studies with Enzalutamide", Clin Pharmacokinet (2015) 54:1057-1069.

Greenblatt et al., "Ritonavir is the best alternative to ketoconazole as an index inhibitor of cytochrome P450-3A in drug-drug interaction studies", Br J Clin Pharmacol 80(3):342-350 (2015).

Guengerich, "Cytochrome P450s and Other Enzymes in Drug Metabolism and Toxicity", The AAPS Journal 2006; 8 (1) Article 12 pp. E101-E111.

Hunt et al., "Identification of the Clinical Candidate (R)-(1-(4-Fluorophenyl)-6-((1-methyl-1H-pyrazol-4-yl)sulfonyl)-,4a,5,6,7,8-hexahydro-1H-pyrazolo[3,4-g]isoquinolin-4a-yl)(4-(trifluoromethyl)pyridin-2-yl)methanone (CORT125134): A Selective Glucocorticoid Receptor (GR) Antagonist", J. Med. Chem. 2017, 60, 3405-3421.

Miners et al., "Cytochrome P4502C9: and enzyme of major importance in human drug metabolism", Br J Clin Pharmacol 1998; 45: 525-538.

Perkins et al., "Physiologically Based Pharmacokinetic Modelling of Cytochrome P450 2C9-Related Tolbutamide Drug Interactions with Sulfaphenazole and Tasisulam", Eur J Drug Metab Pharmacokinet (2018) 43:355-367.

Zanger et al., "Cytochrome P450 enzymes in drug metabolism: Regulation of gene expression, enzyme activities, and impact of genetic variation," Pharmacology & Therapeutics 138 (2013) 103-141.

Canadian Patent Application No. 3178771 , "Office Action", May 23, 2024, 5 pages.

Camanni et al., "The Tolbutamide Test in Cushing's Syndrome", Minerva Medica, vol. 57, No. 1, Jan. 6, 1966, pp. 1-6.

European Patent Application No. 21812189.5 , "Extended European Search Report", May 13, 2024, 13 pages.

Gelmann , "Tamoxifen for the Treatment of Malignancies Other Than Breast and Endometrial Carcinoma", Seminars in Oncology, vol. 24, No. 1, Feb. 1, 1997, pp. S1-65-S1-70.

Hunt et al., "Assessment of Safety, Tolerability, Pharmacokinetics, and Pharmacological Effect of Orally Administered CORT125134:

An Adaptive, Double-Blind, Randomized, Placebo-Controlled Phase 1 Clinical Study", Clinical Pharmacology in Drug Development, vol. 7, No. 4, May 1, 2018, pp. 408-421.

Japanese Patent Application No. 2022-573335 , "Office Action", Mar. 26, 2024, 7 pages.

Lee et al., "Tolbutamide, Flurbiprofen, and Losartan as Probes of Cyp2c9 Activity in Humans", Journal of Clinical Pharmacology, vol. 43, 2003, pp. 84-91.

Munster et al., "Relacorilant (RELA) with nab-paclitaxel (NP): Safety and activity in patients with pancreatic ductal adenocarcinoma (PDAC) and ovarian cancer (OvCA)", Journal of Clinical Oncology, vol. 37, No. 15, May 1, 2019.

Reddy et al., "Prednisolone Induced latrogenic Cushing's Syndrome Associated with Secondary Diabetes: a Case Report", Journal of Basic and Clinical Pharmacy, Jan. 1, 2018, pp. 111-112.

Stearns et al., "Active Tamoxifen Metabolite Plasma Concentrations After Coadministration of Tamoxifen and the Selective Serotonin Reuptake Inhibitor Paroxetine", Journal of the National Cancer Institute, vol. 95, No. 23, Dec. 3, 2003, pp. 1758-1764.

Yuen et al., "Effective Medical Therapy for Cushing Disease Can Increase the Susceptibility to Relative Hypocortisolism", AACE Clinical Case Reports, vol. 4, No. 1, Jan.-Feb. 2018, pp. 1-6.

Chinese Patent Application No. 202180038804.9 , "Office Action", Oct. 29, 2024, 11 pages.

Korean Patent Application No. 10-2022-7045414, "Office Action", Aug. 14, 2025, 10 pages with machine translation.

Ou et al., "Population Pharmacokinetic Analysis of the BTK Inhibitor Zanubrutinib in Healthy Volunteers and Patients With B-Cell Malignancies," Clinical and Translational Science, 2021, pp. 764-772, vol. 14.

Barbot, et al., "Diabetes Mellitus Secondary to Cushing's Disease", Front. Endocrinol, vol. 9, Jun. 5, 2018, pp. 1-8.

Israeli Patent Application No. 298150, "Office Action", Oct. 29, 2025, 7 pages.

Singaporean Patent Application No. 11202260574S, "Written Opinion", Dec. 23, 2025, 11 pages.

Zhang, et al., "Clinical Pharmacology of Cyclophosphamide and Ifosfamide", Current Drug Therapy, vol. 1 No. 1, Jan. 1, 2006, pp. 55-84.

Barbot, et al., "Diabetes Mellitus Secondary to Cushing's Disease", Frontiers in Endocrinology, vol. 9, Jun. 5, 2018, pp. 1-8.

* cited by examiner

CONCOMITANT ADMINISTRATION OF GLUCOCORTICOID RECEPTOR MODULATOR RELACORILANT AND CYP2C9 SUBSTRATES

CROSS-REFERENCE TO RELATED APPLICATION

This application claims priority to, and the benefit of, U.S. Provisional Patent Application No. 63/030,809, filed May 27, 2020, which application is hereby incorporated by reference herein in its entirety.

BACKGROUND

The simultaneous, or nearly simultaneous (e.g., concomitant) presence of two drugs in a subject may alter the effects of one or the other, or both, drugs. Such alterations are termed drug-drug interactions (DDIs). For example, the required dose of a drug is often strongly affected by the amount and rate of its degradation in, and elimination from, the body (e.g., by liver or kidney action). However, the presence of a second drug in the body, which is also being acted upon, e.g., by the liver and kidney, can have significant effects on the amount and rate of degradation of the first drug, and can increase or decrease the amount of the first drug that remains in the body at a given time as compared to the amount that would have been present at that time in the absence of the second drug. Thus, for example, the presence of a second drug that is an inhibitor of an enzyme that metabolizes a first drug will inhibit the metabolism of the first drug and thus can often increase the effective dose of the first drug. Where the first drug has toxic side effects, such an increase in effective dose of the first drug may lead to dangerous toxicity that would not have been expected were the second drug not present.

Concomitant administration of different drugs often leads to adverse effects since the metabolism and/or elimination of each drug may reduce or interfere with the metabolism and/or elimination of the other drug(s), thus altering the effective concentrations of those drugs as compared to the effective concentrations of those drugs when administered alone. Thus, concomitant administration of drugs may increase the risk of toxic effects of one or both of the co-administered drugs.

Cytochrome P450 (abbreviated as CYP or P450) enzymes are hemoproteins of approximately 500 amino acids. Fifty-seven human functional CYP genes have been identified. The human CYP genes are classified into 18 families, designated by a Roman numeral, and 44 subfamilies designated by a capital letter. Classification is based on the amino acid sequence identity of the encoded proteins (Nelson, 2009). Eleven enzymes from CYP families 1, 2 and 3 (CYP1A1, CYP1A2, CYP2A6, CYP2B6, CYP2C9, CYP2C9, CYP2C19, CYP2D6, CYP2E1, CYP3A4 and CYP3A5) primarily contribute to drug and chemical metabolism (Guengerich 208; Zanger and Schwab 2013). These enzymes contribute to the biotransformation of approximately 70% of clinically used drugs. Generally, these enzymes provide a clearance mechanism for drugs and other xenobiotics and facilitate elimination from the body in urine and/or bile. CYP represents one of nature's most versatile enzymes with respect to its broad substrate profile and types of biotransformation reactions. The individual CYP enzymes exhibit distinct, but sometimes overlapping, substrate and inhibitor selectivities. Many drugs inhibit the activity of one or more CYP enzymes, and thus have the potential to cause a drug-drug interaction. Thus, a therapeutic dose of a first drug that is metabolized by a CYP enzyme may become a toxic dose when the first drug is administered with a second drug that inhibits that same CYP enzyme, since the CYP enzyme action on the first drug will be reduced by the presence of the second drug, leading to increased levels of the first drug (as compared to the levels obtained by the same dose of the first drug in the absence of the second drug).

Many therapeutically important drugs are metabolized by the CYP2C9 enzyme. CYP2C9 substrate drugs include, for example, tolbutamide, glimepiride, glipizide, warfarin, benzbromarone, celecoxib, ibuprofen, lornoxicam, meloxicam, and piroxicam. For example, the CYP2C9 substrate tolbutamide (used in treating diabetes) is metabolized by CYP2C9; administration of tolbutamide along with the CYP2C9 inhibitor sulfaphenazole to human subjects led to a more than 5-fold increase in the plasma level of tolbutamide (measured as area under the curve (AUC); Perkins et al., Eur J Drug Metab Pharmacokinet 43(3):355-367 (2018)). Citing similar data regarding tolbutamide, Miners et al. indicated that the current practice is to "individualise" the dose of tolbutamide when used with CYP2C9 substrates (Br J Pharmacol 45:525-538 (2998)).

Relacorilant (see FIG. 1; see also Hunt et al., J. Med. Chem. 60:3405-3421 (2017)) is a selective, non-steroidal modulator of the glucocorticoid receptor that is being investigated in clinical trials in patients with Cushing's syndrome and in patients with various types of cancer including, e.g., pancreatic cancer or ovarian cancer.

SUMMARY

Many therapeutic drugs are substrates of CYP2C9 enzymes; an otherwise safe dose of a first drug metabolized by CYP2C9 may be a toxic dose when concomitantly administered with a second drug that is a CYP2C9 inhibitor. In vitro studies are used to indicate drug combinations expected to suffer from such negative drug-drug interactions (DDIs).

Relacorilant is believed to be useful in treating many disorders, including cancer and hypercortisolism. Relacorilant is further believed to be useful in combination treatments for cancer and in treating hypercortisolism. In vitro tests demonstrated that relacorilant is a potent inhibitor of CYP2C9 ($IC_{50}$ of 2.1 μM). Such potent inhibition of CYP2C9 would be expected to increase plasma exposure of CYP2C9 substrates by more than 5-fold when co-administered with relacorilant. Thus, it was expected that significant reductions in doses of CYP2C9 substrates (e.g., tolbutamide, glimepiride, glipizide, warfarin, benzbromarone, celecoxib, ibuprofen, and others) would be required when administered in combination with relacorilant.

Surprisingly, Applicant determined that it was safe to co-administer relacorilant and a CYP2C9 substrate to human subjects without modifying the dose of the CYP2C9 substrate. Applicant discloses herein that relacorilant may be safely administered along with unmodified doses of tolbutamide, glimepiride, glipizide, and other CYP2C9 substrates, such as, e.g., benzbromarone, celecoxib, ibuprofen, and others. Relacorilant and unmodified doses of tolbutamide, glimepiride or glipizide, and other CYP2C9 substrates may be administered for the treatment of hypercortisolism, or symptoms associated with hypercortisolism. For example, relacorilant and unmodified doses of tolbutamide, glimepiride or glipizide may be administered for the treatment of diabetes associated with hypercortisolism. Applicant's surprising discovery is further believed to apply to cancer patients receiving relacorilant as part of a combination therapy regimen including paclitaxel (e.g., nab-paclitaxel) for the treatment of cancer, such as, e.g., ovarian or pancreatic cancer, or a symptom associated with cancer in a cancer patient. These cancer patients being treated with paclitaxel (e.g., nab-paclitaxel) may benefit from concomitant treatment with relacorilant and tolbutamide, or glimepiride, or glipizide, or other CYP2C9 substrate, and may continue to receive tolbutamide, glimepiride or glipizide, or other CYP2C9 substrate at its therapeutic dose without need for reducing the dose of tolbutamide, glimeprimide, glipizide, or other CYP2C9 substrate concomitantly with relacorilant.

Accordingly, Applicant discloses herein that a CYP2C9 substrate may be concomitantly administered with the selective glucocorticoid receptor modulator relacorilant without reduction in the dose of the CYP2C9 substrate. Such concomitant administration of a CYP2C9 substrate and relacorilant is believed to be safe for the subject and to provide the therapeutic benefits of both drugs to the subject. In embodiments, the CYP2C9 substrate is tolbutamide. In embodiments the CYP2C9 substrate is glimepiride. In embodiments the CYP2C substrate is glipizide. In embodiments, the CYP2C9 substrate may be selected from tolbutamide, glimepiride, or glipizide.

The methods disclosed herein surprisingly provide safe methods for administering drug combinations that were previously expected to be unsafe, allowing concomitant administration of drug combinations with relacorilant. Such drug combinations are believed to provide more effective treatments than treatment with only one of the drugs in the absence of the other. The surprising ability to safely administer these drug combinations provide advantages including more effective treatments, absence of previously expected side effects, and other advantages.

BRIEF DESCRIPTION OF THE DRAWING

FIG. 1 shows the chemical structure of relacorilant ((R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridine-2-yl)methanone).

DETAILED DESCRIPTION

Applicant discloses herein the surprising discovery that relacorilant may be safely co-administered with CYP2C9 substrate drugs without need for reducing the dosage of those CYP2C9 substrate drugs. Such CYP2C9 substrate drugs include tolbutamide, and others. Relacorilant and a CYP2C9 substrate may be co-administered to treat hypercortisolism, e.g., to treat Cushing's syndrome and Cushing's Disease without need for reducing the dosage of the CYP2C9 substrate. The CYP2C9 substrate drug administered with relacorilant to treat hypercortisolism, or a symptom associated with hypercortisolism, such as diabetes, may be, for example, tolbutamide, glimepiride, glipizide, or other CYP2C9 substrate. In embodiments, the CYP2C9 substrate drug is administered with relacorilant to treat hypercortisolism, or a symptom associated with hypercortisolism, is selected from tolbutamide, glimepiride and glipizide. In embodiments, the CYP2C9 substrate drug is administered with relacorilant to treat cancer, or a symptom associated with cancer, in a patient receiving paclitaxel (e.g., nab-paclitaxel) for the treatment of the cancer (e.g., ovarian or pancreatic cancer). The CYP2C9 substrate drug administered with relacorilant to treat cancer, or a symptom associated with cancer, in a patient receiving paclitaxel (e.g., nab-paclitaxel) treatment may be selected from tolbutamide, glimepiride and glipizide.

In embodiments, Applicant discloses a method of treating a disorder, comprising administering to a patient in need of treatment for said disorder:

a) an effective dose of relacorilant; and b) an effective dose of a therapeutic agent, wherein said therapeutic agent is a substrate for CYP2C9 enzyme metabolism, said therapeutic agent having a single agent dose when administered without other pharmaceutical agents, wherein said therapeutic agent effective dose is substantially the same as said single agent dose;

Wherein a) and b) are performed at times effective to provide the patient with an effective level of relacorilant and an effective level of the therapeutic agent at the same time, Whereby the disorder is treated.

In embodiments, the therapeutic agent may be tolbutamide, glimepiride, glipizide, or other CYP2C9 substrate. In embodiments, the disorder is hypercortisolism, or a symptom associated with hypercortisolism, such as diabetes. In embodiments, the disorder is cancer, or a symptom associated with cancer, and the patient is receiving paclitaxel (e.g., nab-paclitaxel) treatment for the cancer, which may be, e.g., ovarian or pancreatic cancer. In embodiments, the therapeutic agent is tolbutamide, glimepiride or glipizide.

Applicant discloses herein that relacorilant may be safely administered along with unmodified doses of CYP2C9 substrates. Applicant discloses herein that relacorilant may be safely administered along with unmodified doses of CYP2C9 substrates such as, e.g., tolbutamide, glimepiride, glipizide, warfarin, benzbromarone, celecoxib, and ibuprofen.

For example, applicant has surprisingly discovered that relacorilant may be administered to subjects concomitantly receiving tolbutamide, glimepiride or glipizide or other CYP2C9 substrate without the need to make dose modifications due to CYP2C9 inhibition. This discovery is surprising, since relacorilant has been shown to be a potent inhibitor of CYP2C9 in vitro and tolbutamide is predominantly metabolized by CYP2C9. However, in a clinical study in healthy volunteers designed to assess the propensity for relacorilant to cause a drug-drug interaction with the CYP2C9 substrate tolbutamide, the expected increase in tolbutamide concentration was not observed, indicating that relacorilant does not inhibit CYP2C9 in a clinical setting.

Applicant's surprising discovery is believed to apply to patients suffering from a disease or disorder and receiving a drug metabolized by CYP2C9. For example, patients receiving tolbutamide, glimepiride, or glipizide for the treatment of a disorder, such as diabetes secondary to hypercortisolism, may benefit from concomitant treatment with tolbutamide, glimepiride or glipizide and relacorilant, and may continue to receive tolbutamide, glimepiride or glipizide at its therapeutic dose without need for reducing the dose of tolbutamide, glimepiride, or glipizide. In a further example, patients receiving tolbutamide, glimepiride or glipizide while being treated for a cancer, such as ovarian or pancreatic cancer, may benefit from concomitant treatment with relacorilant and with tolbutamide, glimepiride or glipizide, and may continue to receive tolbutamide, glimepiride or glipizide at its therapeutic dose without need for reducing the dose of tolbutamide, glimepiride or glipizide while also receiving relacorilant along with their other cancer treatment(s). Such cancer treatments may include paclitaxel (e.g., nab-paclitaxel) treatment.

In embodiments, relacorilant is administered orally. In embodiments, relacorilant, is administered on a daily basis; for example, in embodiments, relacorilant is administered once per day. In embodiments, relacorilant is administered with food. Administered "with food" means that the patient has begun eating a meal within 30 minutes, or within one hour, of the time that relacorilant is administered. For example, relacorilant may be administered to a patient with a meal, or soon after (e.g., within half an hour) the patient began eating the meal.

In alternative embodiments, relacorilant is administered to a fasted patient, i.e., to a patient who has not eaten food for at least one hour, or at least two hours, or more hours prior to relacorilant administration. For example, relacorilant may be administered to a fasted patient in the morning, i.e., to a patient who has not yet eaten the morning meal, and has not eaten since the evening meal of the prior evening.

In embodiments, relacorilant is administered daily, at a daily dose of relacorilant of between about 1 and 100 mg/kg/day, preferably a daily dose of relacorilant of between about 1 and 20 mg/kg/day. In embodiments, the daily dose of relacorilant is between about 10 and about 2000 milligrams (mg), or between about 50 and about 1500 mg, or between about 100 and about 1000 mg relacorilant. In embodiments, a daily dose of relacorilant may be about 10 mg, or 15 mg, or 20 mg, or 25 mg, or 50 mg, or 100 mg, or 150 mg, or 200 mg, or 250 mg, or 300 mg, or 350 mg, or 400 mg, or 450 mg, or 500 mg, or 550 mg, or 600 mg, or 650 mg, or 700 mg, or 750 mg, of 800 mg, or 850 mg, or 900 mg, or 950 mg of relacorilant. In embodiments, an effective relacorilant dose for treatment of hypercortisolism or a disorder associated with hypercortisolism is between about 50 mg/day and about 500 mg/day, and may be, e.g., 150 mg/day, or 200 mg/day, or 250 mg/day, or 300 mg/day, or 350 mg/day, or 400 mg/day. In embodiments, the relacorilant dose may be adjusted (e.g., increased) from an initial dose during the course of treatment.

Definitions

As used herein, the term "patient" refers to a human that is or will be receiving, or has received, medical care for a disease or condition.

As used herein, the terms "administer," "administering," "administered" or "administration" refer to providing a compound or a composition (e.g., one described herein), to a subject or patient. Administration may be by oral administration (i.e., the subject receives the compound or composition via the mouth, as a pill, capsule, liquid, or in other form suitable for administration via the mouth). Oral administration typically involves swallowing the pill, capsule, liquid, or other formulation. Oral administration may include buccal administration (where the compound or composition is held in the mouth, e.g., under the tongue, and absorbed there).

Other examples of modes of administration include, e.g., by injection, i.e., delivery of the compound or composition via a needle, microneedle, pressure injector, or other means of puncturing the skin or forcefully passing the compound or composition through the skin of the subject. Injection may be intravenous (i.e., into a vein); intraarterial (i.e., into an artery); intraperitoneal (i.e., into the peritoneum); intramuscular (i.e., into a muscle); or by other route of injection. Routes of administration may also include rectal, vaginal, transdermal, via the lungs (e.g., by inhalation), subcutaneous (e.g., by absorption into the skin from an implant containing the compound or composition), or by other route.

As used herein, the term "effective amount" or "therapeutic amount" refers to an amount of a pharmacological agent effective to treat, eliminate, or mitigate at least one symptom of the disease being treated. In some cases, "therapeutically effective amount" or "effective amount" can refer to an amount of a functional agent or of a pharmaceutical composition useful for exhibiting a detectable therapeutic or inhibitory effect. The effect can be detected by any assay method known in the art.

As used herein, the terms "co-administration", "concomitant administration", "combined administration", "combination treatment", and the like refer to the administration of at least two pharmaceutical agents to a subject to treat a disease or condition. The two agents may be administered simultaneously, or sequentially in any order during the entire or portions of the treatment period. The at least two agents may be administered following the same or different dosing regimens. Such agents may include, for example, e.g., relacorilant and another drug, which may be, e.g., a drug useful in treating hypercortisolism, may be a drug useful in treating cancer, or another therapeutic agent. In some cases, one agent is administered following a scheduled regimen while the other agent is administered intermittently. In some cases, both agents are administered intermittently. In some embodiments, the one pharmaceutical agent may be administered daily, and the other pharmaceutical agent may be administered every two, three, or four days.

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Therapeutic agents such as relacorilant, tolbutamide, and others, are typically administered in capsules, tablets, or other formulations which include the active agent and one or more pharmaceutically acceptable carriers. The use of such media and agents for pharmaceutically active substances is well known in the art. Except insofar as any conventional media or agent is incompatible with the active compound, use thereof in the compositions is contemplated. Supplementary active agents can also be incorporated into the compositions.

The term "glucocorticoid receptor modulator" (GRM) refers to any compound which modulates GC binding to GR, or which modulates any biological response associated with the binding of GR to an agonist. For example, a GRM that acts as an agonist, such as dexamethasone, increases the activity of tyrosine aminotransferase (TAT) in HepG2 cells (a human liver hepatocellular carcinoma cell line; ECACC, UK). A GRM that acts as an antagonist, such as mifepristone, decreases the activity of tyrosine aminotransferase (TAT) in HepG2 cells. TAT activity can be measured as outlined in the literature by A. Ali et al., J. Med. Chem., 2004, 47, 2441-2452.

Relacorilant (((R)-(1-(4-fluorophenyl)-64(1-methyl-1H-pyrazol-4-yl)sulfonyl)-4,4a,5,6,7,8-hexahydro-1H-pyrazolo [3,4-g]isoquinolin-4a-yl)(4-(trifluoromethyl)pyridine-2-yl) methanone)) is a GRM. Relacorilant is described in Example 18 of U.S. Pat. No. 8,859,774 (hereby incorporated by reference).

As used herein, the term "CYP2C9" refers to the cytochrome P450 enzyme subtype 2C9. In humans, the most common form has 162 amino acids, and has the GenBank accession number AAH70317.1. The gene encoding CYP2C9 has Gene ID 1559.

CYP2C9 substrate drugs include tolbutamide, warfarin, benzbromarone, celecoxib, ibuprofen, glimepiride, glipizide, lornoxicam, meloxicam, piroxicam, and other drugs.

As used herein, a "symptom associated with hypercortisolism" refers to any symptom characteristic of, or often exhibited by, a patient suffering from hypercortisolism. In addition to high cortisol levels, such symptoms include, but are not limited to, diabetes, hypertension, hyperglycemia, abnormal or excessive body fat, moon-face, abnormal blood clotting, depression, and other symptoms.

As used herein, a "symptom associated with cancer" refers to any symptom often exhibited by a cancer patient along with the cancer itself. Such symptoms include, but are not limited to, diabetes, abnormal blood clotting, neutropenia, hypertension, muscle wasting, loss of appetite, depression, and other symptoms.

Example 1. In Vitro CYP Inhibition Assay

Cytochrome P450 (CYP) isoforms CYP1A2, CYP2C9, CYP2C19, CYP2D6, and CYP3A4, heterologously expressed in *E. coli*, were obtained from Cypex and mixed to produce a 5-CYP mix. A selective and FDA accepted substrate for each isoform was present in the reaction at a concentration around its $K_m$.

Relacorilant (final concentration range 0.032-10 μM, 1% DMSO) or a cocktail of control CYP inhibitors was added to reaction tubes in a 96 well plate format. The 5-CYP mix and a CYP substrate cocktail were added and the tubes warmed for 3 minutes whilst mixing on a BioShake IQ (37° C., 1500 rpm). NADPH (final concentration 1 mM) was added and the mixture was incubated for 10 minutes. Methanol containing an internal standard (1 μM tolbutamide) was then added to all samples, and these were mixed and placed at −20° C. for ≥1 hour to quench the reaction and allow protein to precipitate.

All samples were centrifuged (2500×g, 20 minutes, 4° C.). The supernatants were transferred to a fresh 96 well plate, compatible with an autosampler. The plate was sealed with a pre-slit silicone mat and the metabolites were analyzed by LC-MS/MS.

Control CYP inhibitors (IC$_{50}$—appropriate concentration range, final assay concentration 1% DMSO) were added as a cocktail comprised of CYP1A2, α-naphthoflavone (1-0.0032 μM); CYP2C9, sulfaphenazole (10-0.032 μM) CYP2C19, tranylcypromine (100-0.32 μM); CYP2D6, quinidine (1-0.0032 μM); CYP3A4, ketoconazole (0.1-0.00095 μM).

The final concentration in the assay of the 5-CYP mix was 32.5 pmol/ml for each of the enzymes evaluated (i.e., CYP1A2, CYP2C9, CYP2C19, CYP2D6, and CYP3A4).

The CYP substrate cocktail comprised the following components: CYP1A2, tacrine (0.5 μM); CYP2C9, diclofenac (2 μM); CYP2C19, (S)mephenytoin (40 μM); CYP2D6, bufuralol (10 μM); CYP3A4, midazolam (2.5 μM).

The metabolites measured were: CYP1A2, 1-hydroxytacrine; CYP2C9, 4'-hydroxy diclofenac; CYP2C19, 4'-hydroxymephenytoin; CYP2D6, hydroxybufuralol; CYP3A4, 1'hydroxymidazolam.

All reactions were performed in duplicate at 37° C. and in 0.1 M phosphate buffer (pH 7.4). The final protein concentration was 0.12 mg/ml.

Data Processing

Data were processed and the results reported as an IC$_{50}$ value (concentration resulting in a 50% inhibition of response), generated from a pseudo-Hill plot, the slope and y axis intercept being used to calculate the IC$_{50}$ according to the following equation.

$$IC_{50} = 10^{\frac{intercept}{slope}}$$

Relacorilant inhibited CYP2C9 with a mean IC$_{50}$ value of 2.1 μM in this assay.

Based on the in vitro data showing that relacorilant potently inhibited CYP2C9 with a mean IC$_{50}$ value of 2.1 μM, co-administration of a therapeutic concentration of relacorilant with a CYP29 substrate would be expected to result in a greater than 5-fold increase in the plasma exposure of the CYP2C9 substrate, relative to administration of the CYP2C9 substrate alone.

Example 2. Clinical Drug-Drug Interaction Study in Healthy Volunteers

The results of the study described in Example 1 indicated that co-administration of relacorilant and a CYP2C9 substrate to a human subject would lead to large increases in plasma exposure of the CYP2C9 substrate as compared to that CYP2C9 substrate's plasma exposure in the absence of relacorilant.

An open-label, crossover study was conducted in healthy subjects to determine the effect of relacorilant on the plasma exposure of tolbutamide, a known substrate of CYP2C9. A single 500 mg dose of tolbutamide was administered alone and pharmacokinetic (PK) samples were collected before dosing (0 hour) and at 0.5, 1, 1.5, 2, 2.5, 3, 4, 6, 8, 12, 18, 24, 36, and 48 hours post-dose. Relacorilant (350 mg) was then administered once a day for 10 consecutive days. On the following day, a single 500 mg dose of tolbutamide was administered in combination with relacorilant 350 mg and pharmacokinetic (PK) samples were again collected at pre-dose through 48 hours post-dose at the same timepoints as described above. The plasma concentrations of tolbutamide and its metabolite, 4-hydroxy tolbutamide were evaluated by validated bioanalytical assays on each dosing occasion of tolbutamide.

Co-administration of relacorilant with the probe CYP2C9 substrate, tolbutamide, had no effect on tolbutamide AUC$_{0-tz}$ and AUC$_{inf}$ but reduced C$_{max}$ by approximately 31%. Co-administration of relacorilant with tolbutamide also decreased 4-OH tolbutamide C$_{max}$ (by approximately 37%), while having no effect on total 4-OH tolbutamide AUC$_{0-tz}$ and AUC$_{inf}$ The PK results showed that once-daily dosing of relacorilant did not increase the plasma exposures of tolbutamide or its metabolite, indicating a lack of an inhibitory effect of relacorilant on CYP2C9 (Table 1). Although CYP2C9 inhibition by relacorilant had been previously observed in vitro, the surprising results of the clinical drug interaction study demonstrated that relacorilant does not inhibit CYP2C9 in vivo.

TABLE 1

Statistical Comparisons of Plasma Tolbutamide and its Metabolite Pharmacokinetic
Parameters: Day 15 (Treatment E) vs Day 2 (Treatment B) (PK Population)

| Parameter (unit) | Test (Day 15) Treatment E | | Reference (Day 2) Treatment B | | Ratio of | 90% |
| | Geometric LSM | n | Geometric LSM | N | Geometric LSMs (%) | Confidence Intervals |
| --- | --- | --- | --- | --- | --- | --- |
| | Tolbutamide | | | | | |
| $C_{max}$ (ng/mL) | 29370 | 26 | 42430 | 27 | 69.22 | 64.77-73.98 |
| $AUC_{0-tz}$ (ng · h/mL) | 516000 | 26 | 579100 | 27 | 89.11 | 85.71-92.65 |
| $AUC_{inf}$ (ng · h/mL) | 538600 | 26 | 601500 | 26 | 89.54 | 86.02-93.19 |
| | 4-OH Tolbutamide | | | | | |
| $C_{max}$ (ng/mL) | 383.6 | 26 | 604.3 | 27 | 63.49 | 59.48-67.77 |
| $AUC_{0-tz}$ (ng · h/mL) | 7653 | 26 | 8619 | 27 | 88.80 | 86.04-91.65 |
| $AUC_{inf}$ (ng · h/mL) | 8051 | 26 | 8954 | 27 | 89.91 | 87.13-92.79 |

ANOVA, analysis of variance; $AUC_{inf}$, AUC from time 0 extrapolated to infinity; $AUC_{0-tz}$, AUC from time 0 until the time of the last measurable concentration; $C_{max}$, maximum plasma concentration; CV %, coefficient of variation; LSM, least squares mean.

Treatment B: Single oral dose of 500 mg tolbutamide (Reference).

Treatment E: Single oral dose of 500 mg tolbutamide and 350 mg relacorilant administered on Day 15 followed by oral doses of 350 mg relacorilant administered QD on Days 16 and 17 (Test).

Parameters were ln-transformed prior to analysis.

Geometric Least Square means (LSMs) were calculated by exponentiating the LSMs from the ANOVA.

Ratio of Geometric LSMs=100*(Test/Reference); where Test is Treatment E and Reference is Treatment B.

All patents, patent publications, publications, and patent applications cited in this specification are hereby incorporated by reference herein in their entireties as if each individual publication or patent application were specifically and individually indicated to be incorporated by reference. In addition, although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method of treating a disorder selected from the group consisting of i) hypercortisolism, ii) a symptom associated with hypercortisolism in a patient suffering from hypercortisolism, iii) cancer, and iv) a symptom associated with cancer in a cancer patient, said treatment comprising combined administration of tolbutamide and relacorilant to a patient in need of treatment for said disorder, the method comprising administering to said patient in need of treatment for said disorder, without increased tolbutamide plasma exposure to said patient:

a) a 350 milligrams (mg) dose of relacorilant; and
b) 500 mg dose of tolbutamide, wherein said combined administration of relacorilant and tolbutamide does not increase the tolbutamide $AUC_{inf}$ as compared to the tolbutamide $AUC_{inf}$ when administered in the absence of relacorilant, and reduces the tolbutamide $C_{max}$ by an amount that is about 31% of the tolbutamide $C_{max}$ when it is administered in the absence of relacorilant;

Whereby the disorder is treated.

2. The method of claim 1, wherein said disorder is selected from the group consisting of hypercortisolism and a symptom associated with hypercortisolism in a patient suffering from hypercortisolism.

3. The method of claim 2, wherein said symptom associated with hypercortisolism in a patient suffering from hypercortisolism is selected from the group consisting of diabetes, hypertension, hyperglycemia, abnormal body fat, excessive body fat, moon-face, and abnormal blood clotting.

4. The method of claim 3, wherein said symptom associated with hypercortisolism in a patient suffering from hypercortisolism is diabetes.

5. The method of claim 1, wherein said disorder is cancer, or a symptom associated with cancer in a cancer patient.

6. The method of claim 5, wherein the cancer is ovarian cancer or pancreatic cancer.

7. The method of claim 5, wherein said cancer patient is receiving paclitaxel or nab-paclitaxel.

8. The concomitant use of relacorilant and the CYP2C9 substrate tolbutamide in a concomitant treatment, said concomitant treatment comprising concomitant administration of 350 milligrams (mg) of relacorilant and 500 mg of tolbutamide to a patient suffering from and in need of treatment for a disorder, for the treatment of said disorder without increased tolbutamide plasma exposure to said patient, wherein the disorder is selected from the group consisting of hypercortisolism, a symptom associated with hypercortisolism, cancer, and a symptom associated with cancer, wherein said concomitant administration of relacorilant and tolbutamide does not increase the tolbutamide $AUC_{inf}$ as compared to the tolbutamide $AUC_{inf}$ when administered in the absence of relacorilant, and reduces the tolbutamide $C_{max}$ by an amount that is about 31% of the tolbutamide $C_{max}$ when it is administered in the absence of relacorilant, whereby the patient is treated for the disorder.

9. The use of claim 8, wherein said disorder is selected from the group consisting of hypercortisolism and a symptom associated with hypercortisolism.

* * * * *